United States Patent [19]

Schmalzried et al.

[11] Patent Number: 5,378,228
[45] Date of Patent: Jan. 3, 1995

[54] METHOD AND APPARATUS FOR JOINT FLUID DECOMPRESSION AND FILTRATION WITH PARTICULATE DEBRIS COLLECTION

[76] Inventors: Thomas P. Schmalzried, 30428 Calle de Suenos, Rancho Palos Verdes, Calif. 90274; Murali Jasty, 752 Wellesley St., Weston, Mass. 02193

[21] Appl. No.: 809,197

[22] Filed: Dec. 16, 1991

[51] Int. Cl.⁶ .............................................. A61M 27/00
[52] U.S. Cl. .................................... 604/8; 604/9; 604/19; 604/43
[58] Field of Search ............... 604/4, 8, 9, 10, 19, 604/27, 28, 30, 39, 43, 317, 327, 328, 175; 623/12

[56] References Cited

U.S. PATENT DOCUMENTS

| | | |
|---|---|---|
| 3,298,372 | 1/1967 | Feinberg . |
| 3,785,380 | 1/1974 | Brumfield . |
| 3,910,283 | 10/1975 | Leveen ................... 604/9 |
| 4,033,345 | 7/1977 | Sorenson et al. .......... 604/4 |
| 4,772,261 | 9/1988 | Von Hoff et al. ........... 604/175 X |
| 4,822,368 | 4/1989 | Collier . |
| 4,850,964 | 7/1989 | Cotter . |
| 5,019,059 | 5/1991 | Goldberg et al. . |
| 5,100,376 | 3/1992 | Blake, III . |
| 5,102,404 | 4/1992 | Goldberg et al. . |
| 5,120,312 | 6/1992 | Wigness et al. ........... 604/175 |
| 5,222,982 | 6/1993 | Ommaya . |

FOREIGN PATENT DOCUMENTS

| | | |
|---|---|---|
| 0284322A2 | 3/1988 | European Pat. Off. . |
| 2654937A1 | 11/1989 | France . |
| 3343863A1 | 3/1983 | Germany . |
| 4001833A1 | 1/1990 | Germany . |
| 1010067 | 5/1962 | United Kingdom . |
| WO88/01519A1 | 3/1988 | United Kingdom . |

*Primary Examiner*—Sam Rimell
*Attorney, Agent, or Firm*—Robbins, Berliner and Carson

[57] ABSTRACT

Apparatus and methods involving the use of a prosthetic low pressure reservoir for joint fluid and removal of particulate debris from arthritic joints or joints containing artificial, man-made prostheses. The apparatus filters the fluid and traps any particles therein, thus removing them from the periprosthetic space. A communication is created between a space continuous with the articular surfaces of a joint and a separate extraarticular space. The apparatus connects the space continuous with the articular surfaces of the joint to a fluid reservoir located in the extraarticular space. The reservoir contains means for fluid filtration and particle trapping. The extraarticular location of the reservoir is at a lower pressure than the intraarticular space. Increases in intraarticular joint fluid pressure during normal joint activities will cause fluid and particulate debris to preferentially flow into the low pressure reservoir. In this manner, intraarticular fluid pressures are reduced, joint fluid is filtered, and the particulate and/or solute species are collected in the device while joint fluid either diffuses into the extraarticular space or is recycled back into the joint. The device may be implanted at the same time as or any time after a joint is replaced by a prosthesis. This device may also be incorporated as a fixed feature of an implant/bearing combination.

30 Claims, 2 Drawing Sheets

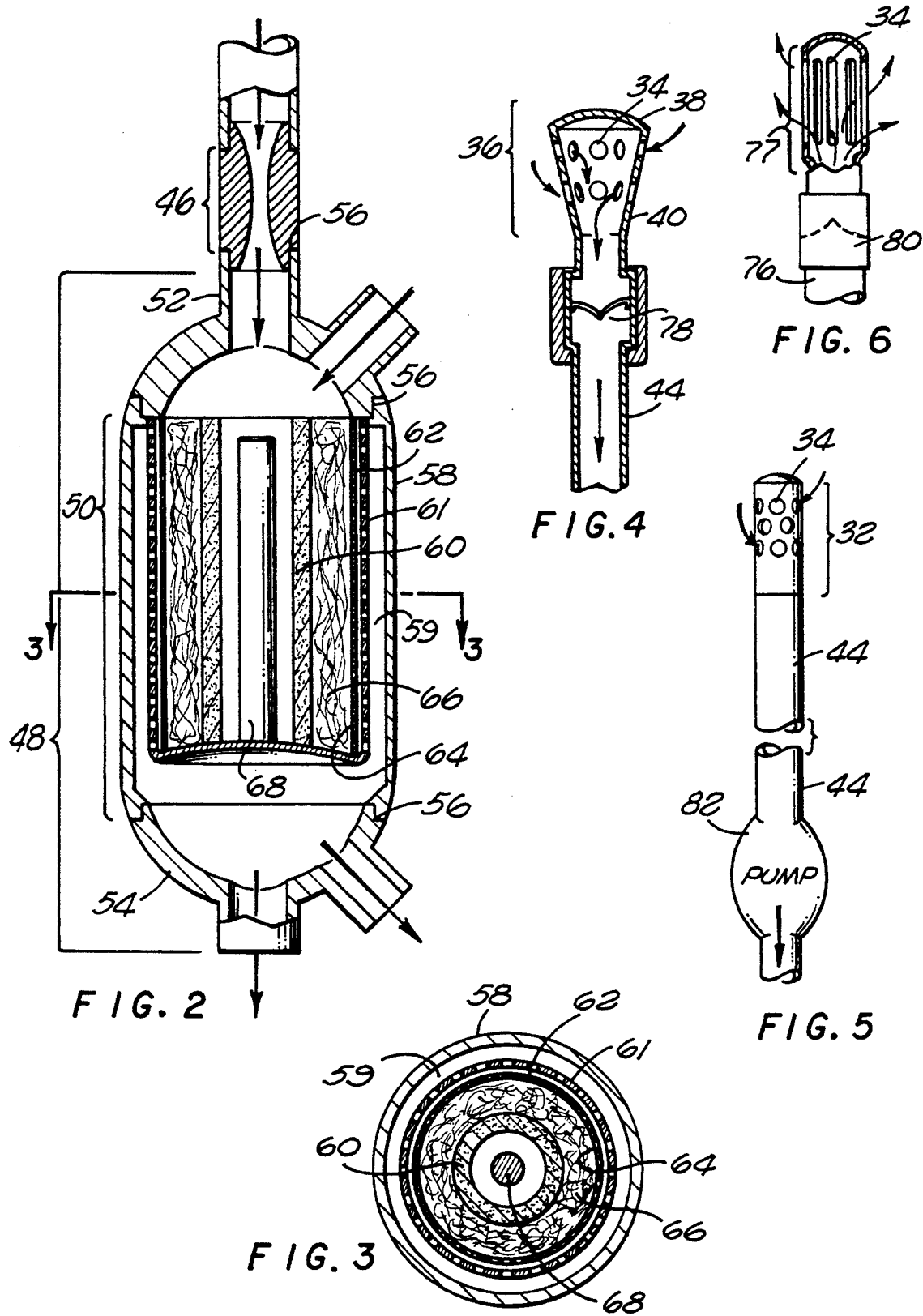

METHOD AND APPARATUS FOR JOINT FLUID DECOMPRESSION AND FILTRATION WITH PARTICULATE DEBRIS COLLECTION

BACKGROUND OF THE INVENTION

The present invention relates generally to the field of orthopaedic surgery and has particular applications in the treatment of arthritic joints and to joints replaced with man-made prosthetic joints.

Normal joints in humans and animals are composed of the ends of two bones which are covered by a smooth gliding surface of articular cartilage. The ends of the bones are linked by a fibrous structure called the capsule which helps stabilize the joint and isolates the joint from the surrounding tissues. The inner surface of the capsule is lined with a thin layer of specialized tissue called the synovium, which in response to motion produces a fluid to lubricate the joint. The space occupied by the fluid is referred to as the joint space. Alternating high and low pressures are produced in the articular cartilage and in the joint fluid during normal use, and are important for joint lubrication.

Normal joints allow repetitive smooth gliding motion over many years. Abnormal or excessive wear, however, results in a pathologic condition generically referred to as arthritis (inflammation of a joint). The cardinal signs of inflammation are pain, warmth, redness, and swelling. In general, this pathologic response is associated with a failure of the natural (articular cartilage) bearing surface of the joint, including wear and fragmentation of the cartilage, and the liberation of the wear products into the joint space. These wear products themselves cause inflammation which further contributes to degradation of the cartilage.

Replacement of the diseased and worn joints with man-made (prosthetic) artificial bearing surfaces has revolutionized the treatment of arthritis over the past thirty years. Most commonly, a metal bearing surface is mated to a plastic bearing surface, although other materials and combinations thereof are possible. The specific geometry of the surfaces is dictated by the anatomy and mechanical functions of the particular joint (hip, knee, shoulder, elbow, ankle, etc.). The prosthetic articulation restores a smooth gliding motion to the joint for a number of years. Following the operation to replace an arthritic joint with an artificial joint, tissue reforms around the articulating surfaces. This tissue is referred to as the pseudocapsule, to distinguish it from the natural capsule. Like the normal capsule, the pseudocapsule synovium produces fluid which lubricates the prosthetic articulation.

The coefficient of friction of these artificial joints is about an order of magnitude greater than that of normal articular cartilage against normal articular cartilage. The heretofore known replacement joint materials comprise metals, plastics, ceramics and other materials. These artificial joints wear, releasing particles of the materials from the prosthetic bearing surfaces into the joints. In a mechanical bearing couple, wear of the bearing surfaces is inevitable and occurs to some extent regardless of the type of materials used. The wear particles can interfere with the smooth motion of the joints and further abrade the smooth surfaces of the joint, thus accelerating the wear and destruction of the articulating surfaces.

In addition to these adverse mechanical factors, it has long been recognized that wear particles liberated into the joint space induce a foreign-body inflammatory response which can result in destruction of bone, and may result in loosening of the prosthesis due to deterioration of the contiguous bone anchors [Willert, H.-G. and Semlitch, M., J. Biomed. Mater. Res. 11, 157–164 (1977)].

Because of the relatively large size of the articular surfaces and the increased amount of particulate wear debris that is generated, surface replacements of the hip have demonstrated a relatively high prevalence of periprosthetic bone resorption, loosening and failure as a result of the inflammatory response to particulate wear debris [Bell, R. S. et al., J. Bone & Joint Surgery 67-A, 1165–1175 (1985); Howie, D. W. et al., Clin. Orthopaedics & Related Res. 255, 144–159 (1990); Nasser, S. et al., Clin. Orthopaedics & Related Res. 261, 171–185 (1990)].

The accumulated information indicates that virtually any material in particulate form can incite a foreign-body inflammatory reaction. The degree of the inflammatory reaction may be related to particle size, composition, shape and number. Small particles (generally those that are less than ten microns in size) are ingested by inflammatory cells called macrophages, while the larger particles are ingested by inflammatory cells called giant cells. When a sufficient number of particles have been ingested, specific cellular processes are initiated resulting in an "activated" macrophage [Murray, D. W., and Rushton, N., J. Bone and Joint Surg. 72-B, 988–992, 1990]. Several substances produced by these cells have been demonstrated to be involved in destroying and resorbing the adjacent bone [Goldring, S. R. et al. J. Bone and Joint Surg. 65-A, 575–583, 1983]. A certain amount of particulate debris can be tolerated and not result in this deleterious reaction. However, when the particles are liberated in sufficient numbers and are of a small enough size, it appears that any prosthetic material can cause macrophage activation. Accordingly, it has been observed that artificial joints that are not heavily used (i.e., that have a low wear rate) have low failure rates compared to artificial joints that are extensively used (i.e., that have a high wear rate).

The role that fluid pressure plays in various arthritic conditions and in bone resorption is becoming increasingly clear. It has been found that joint fluid under pressure may erode into bone and result in the subchondral bone cysts seen in osteoarthritis. Furthermore, in normal and prosthetic joints, there is evidence that there are substantial variations in the fluid pressure both in the space containing the articulating surfaces [Hendrix, R. W. et al., Radiology 118, 647–652 (1983)] and in periprosthetic sites at some distance from the articular surfaces [Anthony, P. P. et al. J. Bone and Joint Surg. 72-B, 971–979 (1990)]. This increased fluid pressure can result in fluid and particle transportation over large distances away from the joint, such as into the distal metaphysis of the femur far below a prosthetic hip joint [Pazzaglia, U. and Byers, P. D., J. Bone and Joint Surg. 66-B, 337–339 (1984)]. The particles collect at these sites and incite an inflammatory reaction in the bone. As described above, this inflammation leads to bone resorption (osteolysis) and can necessitate revision surgery.

It is now recognized that in many artificial joints the range of access for joint fluid and particulate wear debris is much greater than the small space surrounding the articular surfaces. This much larger space can include all the bone and soft tissues adjacent to the prosthesis as well as bone and soft tissues at great distances from the articular surfaces. Polyethylene wear debris has even been identified in the iliac and aortic lymph nodes [Charnley, J., *Low Friction Arthroplasty of the Hip*, New York, Springer-Verlag, pp. 330-331 (1979)]. Thus it is now understood that the joint space can be considered to include all regions, both near and far, that are accessible to joint fluid and particulate wear debris.

While the articular surfaces of a prosthetic joint generally contribute the majority of the particulates, there are other potential sources of particulate debris which include any prosthetic and/or prosthetic-biologic interface where material might be removed by motion and/or corrosion [Svensson, O. et al., *J. Bone Joint Surgery* 70-A, 1238-1242 (1988); Lombardi, A. V. et al., *J. Bone Joint Surgery* 71-A, 1337-1342 (1989)]. Because of communication between the space surrounding the articular surfaces and interfacial planes, debris generated in one location may be transported via the fluid around the prosthesis to another location within the joint space.

Hard particles from the prosthetic implant materials and/or bone debris may be transported by fluid through the joint space into the articulation. The wear of the bearing surfaces is accelerated by the presence of particles of a third material interposed between the two articulating surfaces. All bearing surfaces demonstrate substantially poorer performance in the presence of the third material and the wear pattern which results is called three body wear. A hard particle of any size interposed between the bearing surfaces will act like sand in ball-bearings, no matter how well the two surfaces perform under ideal conditions absent the third material. This accelerated wear creates many more wear particles, producing more inflammation and resulting in further bone resorption.

U.S. Pat. No. 4,822,368 to Collier describes the use of a device to contain wear debris around the articular surfaces so that it does not damage the surrounding tissues. It is proposed that the articular surfaces be isolated by a flexible woven polymer enclosure, which (for the hip joint) is attached on one end to the femoral component and on the other end to the acetabular component. Thus, the articular surfaces are isolated from the adjacent tissues.

While this is an attractive concept, it is fraught with practical problems related to the mechanical nature of the enclosure. Even though the enclosure is flexible to allow the motion of the joint, the femoral neck and the acetabular component can impinge on the enclosure at the extremes of motion and the enclosure can be worn and/or torn. In addition, this device does not remove the wear particles from the articular surfaces. Rather, the wear particles already produced will be ground up in the articulating surfaces, giving rise to smaller and more numerous particles which may become small enough to escape through the enclosure. Additionally, the flexible enclosure itself can undergo fretting with repetitive motion (the hip undergoes approximately one million cycles of motion in a year) and thus itself become another source of wear debris. These particles may also act as third bodies, resulting in accelerated wear of the articulating surfaces. Mechanical failure of such an enclosure would result in the release of the contained particulates into the very region which the device was designed to protect. For these reasons, a system which not only collects particulate debris but also effectively removes the particles from the joint space and traps them so that they cannot escape into the tissues is desirable to minimize both the mechanical and biological problems of particulate debris rather than simply containing the wear particles within the articulation by an enclosure member as proposed in U.S. Pat. No. 4,822,368.

In any mechanical bearing system, whether natural or prosthetic, wear is inevitable. New materials and manufacturing processes may result in bearing surfaces with improved wear characteristics. However, no matter what materials are used, wear of a mechanical bearing cannot be eliminated completely. At best it can be kept to a low level.

The present invention provides methods and apparatus generically applicable to any joint, human or animal, natural or prosthetic, which address both the adverse mechanical effects of wear debris and the adverse biological response (generically referred to as inflammation) to particulate debris in pathological states, such as rheumatoid and osteoarthritis, as well as the particulate debris in prosthetic joints. As low levels of wear are tolerated by most joints, it does not appear to be necessary to capture all of the particulates.

SUMMARY OF THE INVENTION

In accordance with the present invention, a reservoir is provided to receive fluid from a joint through an inflow means. Outflow means are provided for releasing fluid from the reservoir. In various embodiments, there are provided apparatus and methods to reduce joint fluid pressure, filter the joint fluid and trap the particulate debris from arthritic joints and the prosthetic joints used to replace natural joints. An extraarticular low pressure prosthetic reservoir, in communication with the space containing the articular surfaces and/or in any other way in communication with the fluid from the joint, is employed.

The invention capitalizes on intraarticular fluid pressure variations, which occur with normal joint use, to pump fluid and particulate debris into the reservoir. Joint fluid pumped into the reservoir is then filtered. Particulate debris is collected by a trap. A series of traps, specific for certain species of particles, macromolecules, and/or chemicals, may be employed within the reservoir. The filtered joint fluid is then either released into the adjacent extraarticular tissues, is released into some distant location, and/or is recycled back to the articular surfaces. Because of the constant low pressure, the reservoir is the path of least resistance for the flow of joint fluid, and the particles are removed from the joint fluid by the filter/trap. In this manner, the periprosthetic tissues are protected from pathologically high fluid pressures, particulate debris, and the associated adverse tissue reactions (in particular, bone resorption). Additionally, hard particles from any source released into the joint fluid can be carried with the joint fluid into the reservoir and the hard particles collected in the trap, thus reducing the potential for third-body wear.

BRIEF DESCRIPTION OF THE DRAWINGS

The invention will now be described with reference to the accompanying drawings, which are included for purposes of illustration only and should not be considered as in any way limiting the scope of the present invention, in which:

FIG. 2 is a cross-sectional elevational view of the embodiment of the invention shown in FIG. 1;

FIG. 3 is a cross-sectional view of the embodiment of the invention taken along the line 3—3 of FIG. 2;

FIG. 4 is an enlarged, cross-sectional view of an inflow means of the embodiment of the invention shown in FIG. 1;

FIG. 5 is a schematic of an alternative inflow means of the embodiment of the invention shown in FIG. 1; and FIG. 6 is a schematic, partly cross-sectional view of an outflow means of the embodiment of the invention shown in FIG. 1.

DETAILED DESCRIPTION OF PREFERRED EMBODIMENTS

Figure 1:
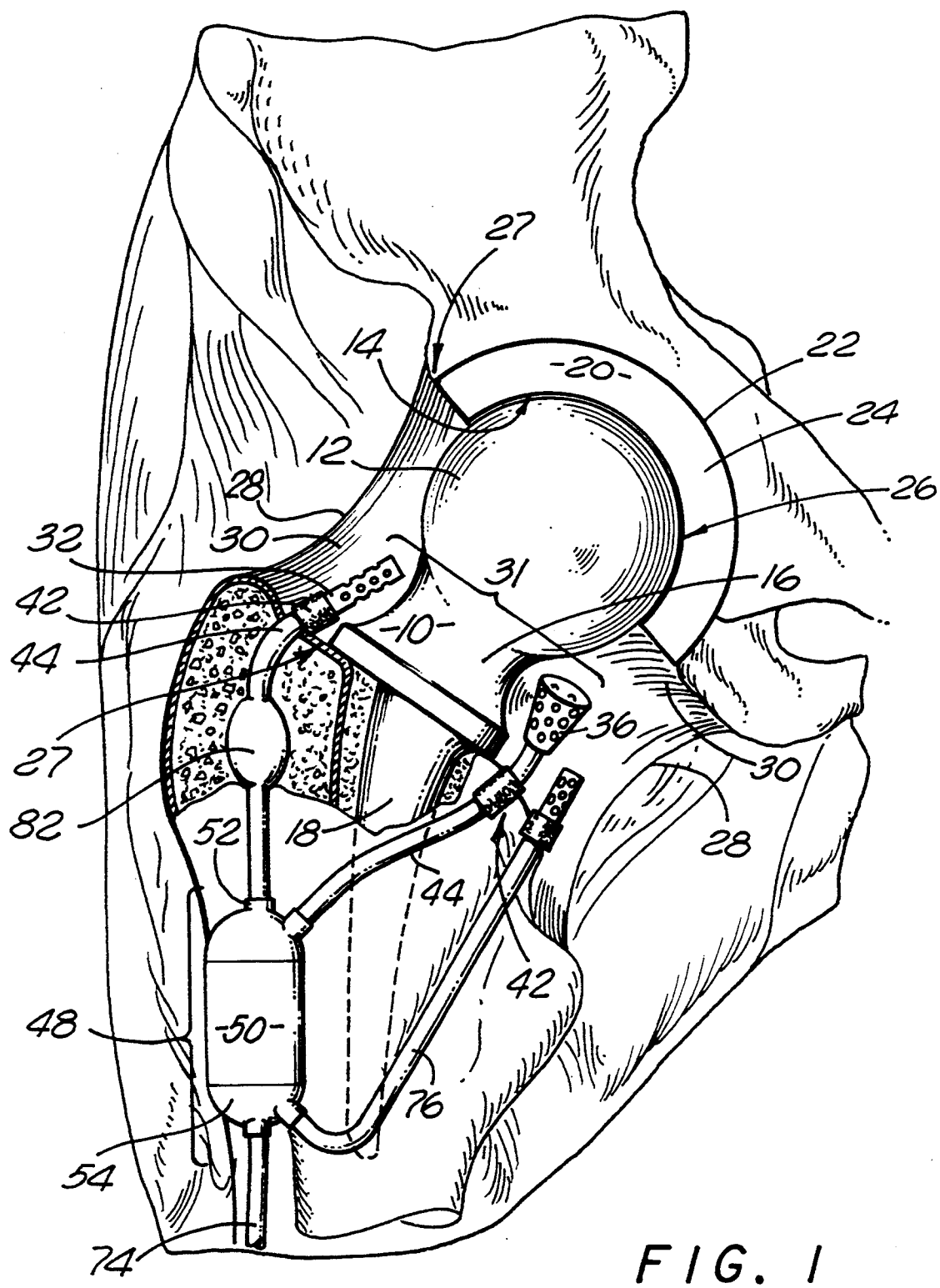
FIG. 1 is a diagrammatic illustration of a human hip joint that has been reconstructed with a conventional (stemmed) total hip replacement and which shows one embodiment of the invention.

Various disease states result in loss of the natural articular cartilage which causes inflammation and pain (arthritis). It has been clearly demonstrated that resection of the diseased natural bearing surfaces and replacement with prosthetic bearing surfaces is highly successful in relieving pain and improving joint function. FIG. 1 shows a generic example of a human hip joint that has been reconstructed with a conventional (stemmed) total hip replacement which includes a femoral component 10 and an acetabular component 20. The femoral component 10 includes a femoral head 12, femoral articular surface 14, femoral neck 16, and femoral stem 18. The acetabular component 20 includes the acetabular shell 22, acetabular body 24, and the acetabular articular surface 26. The natural hip joint is enclosed in a dense soft tissue sleeve called the joint capsule, which is more or less water-tight. During a joint reconstruction, the capsule must be incised and is often resected in whole or in part. If the capsule is only incised or partly resected, then it may be repaired following the joint reconstruction. In any event, a soft tissue layer 28 that is more or less water-tight reforms around the bearing surfaces in response to the motion of the joint. This soft tissue layer 28 is called the pseudocapsule to distinguish it from the original or natural capsule. The pseudocapsule 28 performs several functions which include the formation of joint (synovial) fluid 30 which serves to lubricate the femoral articular and acetabular articular bearing surfaces 14 and 26 and also acts as a collection or storage site for some particulate wear debris. The joint space 31 is that area containing the articular surfaces of the prosthetic implant(s) which is enclosed by the pseudocapsule 28 as well as any other areas to which the fluid 30 may flow. The hip joint is covered by several large muscles (not pictured). Contraction of these muscles and changes in joint position result in compression of the pseudocapsule 28 and variations in the intraarticular fluid pressure.

The fluid around prosthetic joints contains many different solid materials, including non-biologic material such as wear particles from the prosthesis which can be composed of various metals, polymers, ceramics, etc. The fluid also contains different solid materials which are biologic in origin including bone fragments, crystals, cells and portions of cells. Generically, these are all "solid species". Joint fluid also contains various proteins and chemicals, which include proteinases and inflammatory mediators, which are dissolved, or "in solution." Generically, these are all "solute species."

FIG. 1 shows the preferred embodiment of the invention which generally comprises a low pressure sink or reservoir 48 having one or more inflow portals 32 in communication with the joint fluid 30. The various components of the preferred embodiment are made of biocompatible materials such as polymers and/or metals. Many different materials are suitable for this purpose, such as stainless steel, titanium or cobalt based alloys, polysulfone, polyurethane, polyethylene, polyacetal, and/or polytetrafluoroethylene.

The apparatus of the preferred embodiment has an inflow portal 32 located in the joint space 31 or otherwise in communication with the joint fluid 30. The inflow portal 32 can be located immediately adjacent to the bearing surfaces 14 and 26, yet it does not inhibit motion nor in any other way interfere with the mechanical function of the joint. Being located close to the moving parts insures that the inflow portal 32 will not become covered by soft tissue. The inflow portal 32 may have a wide range of shapes and sizes depending on the specific location and joint involved. While a variety of different shapes and designs for the inflow portal would be suitable for use in accordance with the present invention, the inflow portal should have a size and shape such that occlusion of the inflow portal 32 by particulate materials is essentially obviated.

As an example, in the human hip joint, the inflow portal 32 may be cylindrical in shape with an internal diameter ranging from one to twenty millimeters. In one preferred embodiment, as shown in detail in FIG. 5 (for the human hip joint), the inflow portal 32 comprises a flexible biocompatible polymer and is cylindrical in shape with a five millimeter inner diameter. The walls of the inflow portal may have fenestrations 34 of a lesser diameter (ranging from one-half millimeter to three millimeters in this embodiment) in order to increase fluid access to the interior of the inflow portal 32. In another embodiment shown in FIG. 4, the inflow portal 36 is funnel shaped, having an internal diameter of fifteen millimeters at the mouth 38 and five millimeters at the apex 40. This inflow portal may also have fenestrations 34. As would be readily apparent to one skilled in the art, alternative embodiments would be equally suited for particular uses with various joints or for other purposes. In order to increase the amount of fluid collected, multiple inflow portals at various locations within the same joint may be used, as is shown in FIG. 1.

The inflow portal 32 may enter the joint space through bone and/or soft tissue. The inflow portal 32 is secured in the joint space by an interference fit or mechanical fastening to the surrounding bone or soft tissue of the entrance site. One suitable method of fixation comprises a porous sleeve 42 fitted around the base of inflow portal 32, which allows tissue ingrowth for long-term stability. Other methods of fixation are of course equally suitable, the salient concern being to create and maintain a seal between the inflow portal and the tissues of the entrance site.

The inflow portal 32 is connected to an inflow conduit 44 which is flexible but non-compressible. The inflow conduit 44 connects the inflow portal 32 to the reservoir 48, as described in greater detail hereinafter. The inflow conduit 44 may vary over a fairly broad range with respect to internal diameter and length. Typically, the inflow conduit 44 has an internal diameter roughly corresponding to the internal diameter of the inflow portal 32. In the example above, this would be about five millimeters. In various embodiments of the device, the associated reservoir 48 may be immediately adjacent to the inflow portal or located at some distance from the inflow portal 32. Accordingly, it is contemplated that the inflow conduit 44 could have a length ranging from less than one millimeter to as long as 50 centimeters. In the preferred embodiment described, the inflow conduit 44 would be a cylindrical tube composed of a biocompatible polymer or metallic alloy of length between ten and fifteen centimeters.

Having the smallest cross-sectional area in the system, the resistance to flow of fluid and particles through the device is primarily determined by the inner diameter of the inflow 44 and outflow 74, 76 conduits and secondarily by the length of these conduits. In general, larger diameters and shorter lengths (as dictated by the joint under consideration) will decrease the resistance to fluid flow through the device. In some cases, however, it may be desirable to provide a section of a conduit to function as a resistor 46 in order to avoid overdrainage of joint fluid. Any portion of a conduit with a reduced cross-sectional area would function as such a resistor. FIG. 2 shows a short conduit section of smaller diameter at the attachment site to the inflow couple 52 which would form a resistor 46. Alternatively, the resistor 46 could be placed at the outflow couple 54. The degree of resistance would of course be determined by the internal diameter of this short conduit section. Alternatively, a short section of the conduit(s) could be made slightly more compliant in order to allow external compression by a mechanical fastening. This mechanical fastening could take the form of a constricting non-absorbable surgical suture, a constricting metallic ring, clamp, etc. The degree of resistance would of course be variable as determined by the amount of constriction of this compliant section.

The construction of the reservoir 48 is shown in detail in FIG. 2 and consists of a body 50 and inflow couple 52 and outflow couple 54. The reservoir 48 functions as a prosthetic low pressure sink. To function as a low pressure sink, the reservoir is located in an extraarticular location where the mean hydrostatic pressure is lower than the intraarticular fluid pressure. The reservoir 48 may be secured to the adjacent tissues by a variety of means, such as suturing or other mechanical fastening, and/or by adding a porous material to the outer shell which would allow tissue ingrowth. The reservoir may thus be located in bone, in soft tissue, or within the structure of a prosthetic joint implant. The dimensions would of course vary depending upon the intended use. It is contemplated that a reservoir 48 having an internal volume ranging from less than 0.125 cubic millimeters up to 125 cubic centimeters would be suitable for use for most purposes. The particular shape of the reservoir 48, as well as the specific dimensions thereof, would of course not be critical to practice of the present invention. As an example, a simple cylindrical or capsular shape would be satisfactory.

The inflow couple 52 and outflow couple 54 of the reservoir 48 may be modular and connected to the body of the reservoir 50 and to the inflow 44 conduit and the outflow conduits 74, 76 by an interference fit 56 or other mechanical fastening. Modular construction allows variability of connections to the inflow conduit 44 and to the outflow conduits 74, 76, as well as allow access to the interior and contents of the reservoir 48.

In the preferred embodiment as shown in detail in FIGS. 2 and 3, the reservoir 48 typically comprises an outer compression-resistant shell 58 with an interior construction comprising at least one cylindrical inner screen filter 60, a cylindrical trap space 64, a cylindrical semipermeable membrane liner 62, and a fenestrated cup-shaped support plate 61 for the semipermeable membrane liner 62. The inner screen filter 60 filters particles and supports any medium, such as a porous material 66 in the trap space 64. The outer shell 58 functions as a protective casing which resists external compression and insures that the interior of the reservoir functions as a low-pressure sink. The interior construction of the reservoir provides a filter mechanism which allows for separation of the solid particulate debris from the liquid portion of the joint fluid. In order to filter tissue debris and large particles, the size of the inner screen filter fenestrations would be on the order of 0.05 to two millimeters. To improve filtration efficiency, a series of inner screen filters, each with a different size fenestration, could also be employed.

The semipermeable material of the liner allows fluid, and macromolecules which exert a colloid pressure, to pass but does not permit the passage of particles which are greater than of a submicron size. It should be obvious that a series of semipermeable membrane liners could be used in conjunction with a serial inner shell construction. The cup-shaped support plate 61, having fenestrations on the order of 0.01 to 0.05 millimeters, allows unrestricted passage of fluid, but not tissue debris or large particles, and provides a rigid support housing for the semipermeable membrane liner(s) 62. Suitable materials for the outer compression-resistant shell 58 and inner screen filter 60 and the cup-shaped support plate 61 include biocompatible polymers or metallic alloys. Suitable materials for the semipermeable membrane liner 62 include cellulose acetate with a maximum pore size between fifty and 100 angstroms.

In preferred embodiments of the invention, the reservoir 48 may contain additional mechanism(s) such as the central tubular core 68 to separate solid particulate debris and/or a solute species from the joint fluid 30. Examples of species-specific filtration mechanisms include, but are not limited to, the following: magnetic materials for metal particles; charcoal and/or reverse osmosis technology for ions; and adsorptive material for forming ionic and/or chemical bonds with molecular ligands. Further, it should be readily apparent that filter means may be contained in any part of the assembly.

In preferred embodiments of the invention, the reservoir 48 includes at least one space 64 to collect and contain particulate (solid) and/or non-particulate (solute) species. The particle trap 64 may, for example, be filled with a porous material 66. As fluid flows into the reservoir, particles become entangled or trapped in the three-dimensional fiber-weave of the porous material 66. The pore sizes of the material(s) determine the range of particle sizes to be trapped. In this manner, a variety of particle sizes can be trapped. Suitable pore sizes in accordance with the present invention range from 100 angstroms to 300 microns. The porous material 66 is made of one or more biocompatible polymers, such as polyurethane, polysulfone, and/or cellulose. A combination of particle traps which are particle-specific may be used. Materials with differing pore sizes may be assembled in series to trap particles of a broad range of sizes. Species-specific particle traps include, but are not limited to, the following: magnetic materials for metal particles; charcoal and/or reverse osmosis technology for ions; and adsorptive material for forming ionic and-/or chemical bonds with macromolecular ligands, such as immunoglobulins and/or chemical mediators, such as prostaglandins and/or interleukins. For example, in cases where metal debris is expected, the specific particle trap is suitably constructed with magnetic materials. These include materials made of iron or cobalt alloys, as well as colloidal suspensions of magnetic particles. The metal particles are trapped within the magnetic portion of the reservoir thus removing them from the joint space and periprosthetic tissues. Various components of the inner contents of the reservoir 48 may be made modular in order to be exchangeable and replaceable, and to allow various combinations of elements.

In operation, joint fluid 30 flows into the inflow portals 32, 36 and by way of inflow conduits 44 to the reservoir 48. Fluid then flows over the tubular core 68 and through the screen filter 60, trap space 64 containing porous material 66, semipermeable membrane liner 62, and out through the fenestrations in support plate 61. The fluid then enters the reservoir space 59 and exits the reservoir 48 by way of outflow conduits 74, 76.

Fluid egress from the reservoir occurs by means of outflow conduits 74, 76 connected to the outflow couple 54 of the reservoir 48. The outflow conduits 74, 76 are of sufficient size so as to not provide resistance to fluid flow out of the reservoir 48 and are similar in design and construction to the inflow conduit 44. In the described embodiment shown in FIG. 6, this would comprise a cylindrical tube of five millimeters inner diameter composed of a biocompatible polymer or metallic alloy. The end of the outflow conduit 77 may contain fenestrations 34. Linear fenestrations 34, shown in FIG. 6, are on the order of 0.5 to 3 millimeters by 2 to 6 millimeters. The outflow conduit 74 may simply release the filtered fluid into the tissues around the reservoir. Alternatively, an outflow conduit may transport the filtered fluid to some site at a great distance from the joint, such as the abdominal-peritoneal cavity. In one embodiment, the filtered fluid may be transported via an outflow conduit 76 to the space containing the articular surfaces of the joint 31 as shown in FIG. 1 Accordingly, it is contemplated that the outflow conduits 74, 76 would typically have a length in a range from less than one millimeter to as long as 200 centimeters. Multiple outflow conduits may be used to distribute the filtered joint fluid to various locations.

The invention may further comprise one or more valves 78, 80 to assure directional flow as are shown in FIGS. 4 and 6. These valves could take the form of simple leaflets such as the unidirectional valves in the mammalian venous system and could be composed of a biocompatible polymer. In one embodiment, an inflow valve 78 located near the inflow portal 32 opens when the pressure inside the joint space is high to allow fluid and particles to flow into the inflow conduit 44 and then closes when the pressure inside the joint space is low. The transient increases in fluid pressure drives fluid and particulate debris into the reservoir 48. Due to the filter mechanism and particle traps, fluid but not particles exits the reservoir 48 through the outflow conduit(s) 74, 76. When the pressure inside outflow conduit 76 is greater than the pressure in the joint space 31, an outflow valve 80 in the outflow conduit 76 then opens. In this manner, filtered joint fluid may be recycled back to the articulating surfaces 14, 26 for lubrication.

It may be necessary to periodically flush fluid and debris through the device. One means to accomplish this would be a simple pump mechanism 82 (FIG. 5) involving a fusiform expansion about two or three centimeters in length in a section of the inflow conduit 44. The inner diameter of this section would be roughly two to four times the inner diameter of the remainder of the inflow conduit (one to two centimeters in the preferred embodiment). The expanded pump section 82 could be composed of a biocompatible polymer. The material of the pump section would have an increased compliance compared to the remainder of the inflow conduit 44. In this manner directed external compression onto the pump would compress this expanded pump section 82 of the inflow conduit 44, thereby increasing the fluid pressure within the device and flushing fluid through the device. Alternatively, a sterile fluid such as normal saline could be percutaneously injected into the pump section 82 in order to flush fluid and debris through the device. It should be apparent that such a pump mechanism, or other means to flush fluid through the device, could equally well be incorporated into the outflow conduit system or other portion of the device.

Preferred embodiments of the inventive apparatus may be inserted without opening the joint, and the component parts of the apparatus are modular and exchangeable. Filters and particle traps can be exchanged or changed, the resistance to fluid flow modified, and the outflow site of filtered fluid changed in an essentially routine manner, and in some instances without serious invasive surgery.

There are many sites which are possible for the location of the device. In accordance with one preferred embodiment of the invention, the device is incorporated into a prosthetic joint component. Using the hip as an example, the device of the present invention may be incorporated into the prosthetic femoral head 12, the prosthetic femoral neck 16, the stem of the femoral component 18, the body of the acetabular component 24 and/or physically attached to any of the prosthetic components. In this embodiment, the inflow and outflow portals take the form of holes within the prosthetic joint components and the conduits may then be very short. The reservoir with the particle traps may then be contained within the prosthetic joint components. Such an incorporation into an artificial joint has applications in any mammalian joint. Further, such an incorporation would also have application in all resurfacing-type artificial joints for the hip as well as for the knee. Exchange of the filters and traps in these instances may require opening of the joint space through a capsulotomy. However, relative to existing technology, the ability to manufacture the prosthesis with the devices already built into them provides a significant advantage. When the inventive device is incorporated into a prosthetic joint component, it is of course important that the overall integrity of the prosthetic device not be compromised.

Alternatively, the device can be fabricated into different shapes so as to be positioned adjacent to the articular surfaces within the joint space 31 and covering and/or be within the bone-prosthesis interfaces 27. In this embodiment, the device has shapes specific for the site of application. Again, the inflow and outflow portals may take the form of holes within the reservoir and the conduits may be very short. In this type of embodiment, the particles are trapped just before they have access to the interface between the bone and the prosthesis (where they are likely to do the most damage). In cases with established localized bone resorption (osteolysis), an inflow portal 32 may be placed directly into the area of lysis. In this manner, both the fluid pressures and the particle load in this region are decreased. As has been shown, there is great flexibility in the design and fabrication of the inventive apparatus.

In addition to reducing intraarticular fluid pressures, the apparatus and methods of the present invention serve the salutary purpose of collecting particulate debris of any species. Elimination of this debris reduces third-body wear, while not interfering with the mechanical function of the joint. It is of particular advantage that the present invention simultaneously addresses both third-body wear problems resulting from particulate debris and the increased fluid pressures from the particulate induced synovitis. The inventive apparatus relies on fluid-pressure changes generated by normal joint use, and contains no or few moving parts. As a consequence, the present invention is adaptable to a wide variety of different applications and structural embodiments. The device may be implanted at the same time as or any time after a joint is replaced by a prosthesis. This device may also be incorporated as a fixed feature of an implant/bearing combination.

It is to be understood that both the foregoing detailed description is exemplary and explanatory but not restrictive of the invention. In particular, while a hip prosthesis is used for illustrative purposes, the features of the invention are described in a generic form such that they would be applicable to the geometric and biomedical properties of all animal and human joints and to all joint prostheses.

While there have been shown and described the fundamental novel features of the invention, it will be understood that various omissions, substitutions and changes in the form and details of the contraceptive devices illustrated may be made by those skilled in the art without departing from the spirit of the invention.

What is claimed is:

1. An apparatus for fluid decompression and solid and solute species collection from mammalian joints, comprising:
    inflow means in communication with said joint for receiving fluid and solid and solute species from said joint;
    a low pressure reservoir in communication with said inflow means for receiving said fluid and said solid and solute species;
    filter means internal to the reservoir for separating said solid and solute species from said fluid; said filter means including a semipermeable membrane and a core filtration means spaced from said membrane;
    outflow means in communication with said reservoir for releasing said fluid from said reservoir,
    wherein said apparatus is biocompatible and implantable in a mammalian joint.

2. The apparatus according to claim 1, further comprising collecting means for collecting said solid and solute species separated from said fluid by said filter means.

3. The apparatus according to claim 2, further comprising trapping means for containing said solid and solute species collected by said collecting means.

4. An apparatus according to claim 3, wherein the inflow means comprises an opening of said reservoir into said joint to allow ingress of fluid and solid and solute species into the reservoir.

5. An apparatus according to claim 4, wherein the inflow means further comprises an inflow conduit connecting the inflow means and the reservoir.

6. An apparatus according to claim 5, wherein the reservoir comprises an incompressible outer shell and an inner semipermeable membrane-liner, and the pressure in the reservoir is lower or equal to the fluid pressure in the joint.

7. An apparatus according to claim 6, wherein the reservoir further comprises at least one inflow valve to allow the fluid and the solid and solute species to enter the inner shell and the filter.

8. An apparatus according to claim 7, wherein the reservoir further comprises at least one outflow valve to allow release of the fluid after filtering.

9. An apparatus according to claim 8, wherein said trapping means comprises a particle trap to allow the fluid to flow out of the reservoir but contain the solid and solute species within the reservoir.

10. An apparatus according to claim 1, wherein the outflow means comprises an outflow conduit to return the fluid to the joint.

11. An apparatus according to claim 10, wherein the outflow conduit comprises a valve which opens to the joint when pressure inside the joint is low, the valve being otherwise closed.

12. An apparatus according to claim 11, wherein said inflow conduit comprises a flexible tube.

13. The apparatus according to claim 1 wherein said apparatus or one or more parts thereof can be incorporated into a prosthetic joint component.

14. A method for synovial fluid decompression and solid and solute species collection from mammalian joints, comprising:
    receiving synovial fluid and solid and solute species from said joint into a low pressure reservoir;
    separating said received fluid from said received solid and solute species; and
    releasing said fluid from said reservoir, while said reservoir retains said solid and solute species.

15. A method according to claim 14, further comprising collecting said separated solid and solute species.

16. A method according to claim 15, further comprising containing said collected solid and solute species.

17. A method according to claim 16, further comprising returning the fluid released from said reservoir to the joint.

18. An apparatus to collect and filter fluid and solid and solute species from mammalian joints, comprising:
    inflow means in communication with said joint for receiving fluid and associated solid and solute species from said joint;
    a reservoir in communication with said inflow means for receiving said fluid and associated solid and solute species, said reservoir providing a low pressure sink;
    outflow means in communication with said reservoir for releasing said fluid from said reservoir; and
    filter means adapted to separate solid and solute species from said fluid, said filter means including a semipermeable membrane and filtration means spaced from said membrane;
    wherein said apparatus is biocompatible and implantable in a mammalian joint.

19. The apparatus according to claim 18, further comprising collecting means adapted to collect solid and solute species separated from said fluid by said filter means.

20. The apparatus according to claim 19 further comprising trapping means adapted to contain solid and solute species collected by said collecting means.

21. The apparatus according to claim 20 wherein the trapping means comprises means for separating specific solid and solute species from said fluid.

22. The apparatus according to claim 21 wherein the means for separating specific solid and solute species from said fluid comprises mechanical means.

23. The apparatus according to claim 21 wherein the means for separating specific solid and solute species from said fluid comprises osmotic means.

24. The apparatus according to claim 21 wherein the means for separating specific solid and solute species from said fluid comprises chemical means.

25. The apparatus according to claim 21 further comprising means for releasing the fluid into locations outside of said reservoir, including the location where the fluid was received.

26. The apparatus according to claim 25 further comprising means for providing directional fluid flow.

27. The apparatus according to claim 26 further comprising means for increasing the resistance to fluid flow through said apparatus.

28. An apparatus to collect and filter fluid and solid and solute species from mammalian joints, comprising:
   inflow means in communication with said joint for receiving fluid and associated solid and solute species from said joint;
   a reservoir in communication with said inflow means for receiving said fluid and associated solid and solute species, said reservoir providing a low pressure sink;
   outflow means in communication with said reservoir for releasing said fluid from said reservoir;
   filter means adapted to separate solid and solute species from said fluid, wherein said apparatus is implantable;
   collecting means adapted to collect solid and solute species separated from said fluid by said filter means;
   trapping means adapted to contain solid and solute species collected by said collecting means, wherein said trapping means includes means for separating specific solid and solute species from said fluid;
   means for releasing the fluid into locations outside of said reservoir, including the location where the fluid was received;
   means for providing directional fluid flow;
   means for increasing the resistance to fluid flow through said apparatus; and
   means for periodically flushing fluid and associated solid and solute species through the apparatus.

29. An apparatus to collect and filter fluid and solid and solute species from mammalian joints, comprising:
   inflow means in communication with said joint for receiving fluid and associated solid and solute species from said joint;
   a reservoir in communication with said inflow means for receiving said fluid and associated solid and solute species, said reservoir providing a low pressure sink;
   outflow means in communication with said reservoir for releasing said fluid from said reservoir;
   filter means adapted to separate solid and solute species from said fluid, wherein said apparatus is implantable;
   collecting means adapted to collect solid and solute species separated from said fluid by said filter means; and
   trapping means adapted to contain solid and solute species collected by said collecting means, wherein said trapping means includes means for separating specific solid and solute species from said fluid; wherein the means for separating specific solid and solute species from said fluid comprises magnetic means.

30. An apparatus to collect and filter fluid and solid and solute species from mammalian joints, comprising:
   inflow means in communication with said joint for receiving fluid and associated solid and solute species from said joint;
   a reservoir in communication with said inflow means for receiving said fluid and associated solid and solute species, said reservoir providing a low pressure sink;
   outflow means in communication with said reservoir for releasing said fluid from said reservoir;
   filter means adapted to separate solid and solute species from said fluid, wherein said apparatus is implantable;
   collecting means adapted to collect solid and solute species separated from said fluid by said filter means; and
   trapping means adapted to contain solid and solute species collected by said collecting means, wherein said trapping means includes means for separating solid and solute species from said fluid; wherein the means for separating specific solid and solute species from said fluid comprises ionic means.

* * * * *